(12) United States Patent
Daniele et al.

(10) Patent No.: US 12,121,687 B2
(45) Date of Patent: Oct. 22, 2024

(54) NANOCELLULOSE AND NANOCELLULOSE COMPOSITE ARRAYS AND DEVICES AND METHODS OF MAKING AND USING THE SAME

(71) Applicant: North Carolina State University, Raleigh, NC (US)

(72) Inventors: Michael Daniele, Raleigh, NC (US); Ethan Marrow, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 611 days.

(21) Appl. No.: 16/647,110

(22) PCT Filed: Sep. 18, 2018

(86) PCT No.: PCT/US2018/051600
§ 371 (c)(1),
(2) Date: Mar. 13, 2020

(87) PCT Pub. No.: WO2019/056020
PCT Pub. Date: Mar. 21, 2019

(65) Prior Publication Data
US 2020/0230388 A1 Jul. 23, 2020

Related U.S. Application Data

(60) Provisional application No. 62/559,993, filed on Sep. 18, 2017.

(51) Int. Cl.
*A61M 37/00* (2006.01)
*A61B 5/15* (2006.01)
(Continued)

(52) U.S. Cl.
CPC ... *A61M 37/0015* (2013.01); *A61B 5/150984* (2013.01); *A61M 2037/0053* (2013.01);
(Continued)

(58) Field of Classification Search
CPC ...... A61M 37/0015; A61M 2037/0053; A61M 2037/0061; A61M 2207/10; A61B 5/150984
(Continued)

(56) References Cited

U.S. PATENT DOCUMENTS

2003/0069548 A1* 4/2003 Connelly .......... A61M 37/0015
606/186
2009/0182306 A1 7/2009 Lee et al.
(Continued)

OTHER PUBLICATIONS

"Microneedles from Fishscale-Nanocellulose Blends Using Low Temperature Mechanical Press Method" by Ololade Olatunji (Year: 2015).*
(Continued)

*Primary Examiner* — Phillip A Gray
(74) *Attorney, Agent, or Firm* — THOMAS | HORSTEMEYER, LLP (57) ABSTRACT

A microneedle array including a plurality of microneedles that include nanocellulose or a nanocellulose composite, methods of producing a microneedle array, a device including a microneedle array, and methods of extracting a dermal biofluid or subdermal biofluid by applying a microneedle array.

20 Claims, 9 Drawing Sheets

(51) Int. Cl.
   *B82Y 5/00* (2011.01)
   *C08L 1/02* (2006.01)
(52) U.S. Cl.
   CPC . *A61M 2037/0061* (2013.01); *A61M 2207/10* (2013.01); *B82Y 5/00* (2013.01); *C08L 1/02* (2013.01)
(58) Field of Classification Search
   USPC .......................................................... 604/272
   See application file for complete search history.

(56) References Cited

U.S. PATENT DOCUMENTS

| | | |
|---|---|---|
| 2011/0152792 A1 | 6/2011 | Takada |
| 2014/0200508 A1 | 7/2014 | Cohen et al. |
| 2015/0044708 A1 | 2/2015 | Hussa et al. |
| 2015/0202418 A1 | 7/2015 | Simon et al. |
| 2016/0001053 A1* | 1/2016 | Quan ................ A61M 37/0015 427/2.31 |
| 2016/0045720 A1* | 2/2016 | Suzuki .............. A61M 37/0015 264/485 |
| 2019/0245155 A1* | 8/2019 | Heath ................. H10K 85/731 |

OTHER PUBLICATIONS

International Search Report and Written Opinion for International Application No. PCT/US18/51600, mailed Dec. 10, 2018.

\* cited by examiner

| Film | Water Uptake (wt%) |
|---|---|
| 2% HA | 432 |
| 1%/1% HA + TEMPO | 647 |
| 4% HA | 374 |
| 2%/2% HA + TEMPO | 424 |

NANOCELLULOSE AND NANOCELLULOSE COMPOSITE ARRAYS AND DEVICES AND METHODS OF MAKING AND USING THE SAME

CROSS-REFERENCE TO RELATED APPLICATIONS

This patent application is the U.S. national stage entry, under 35 U.S.C. § 371, of International Application Number PCT/US2018/051600, filed Sep. 18, 2018, which claims the benefit of the earlier filing date of U.S. Provisional Application No. 62/559,993, filed Sep. 18, 2017, the entire contents of each of which are hereby incorporated by reference.

STATEMENT REGARDING FEDERALLY SPONSORED RESEARCH

This invention was made with government support under grant number 1160483 awarded by the National Science Foundation. The government has certain rights to this invention.

TECHNICAL FIELD

The present disclosure pertains to materials system designs for devices such as microneedle-based arrays comprising nanocellulose or nanocellulose composites, methods of manufacturing the same, as well as methods for extracting dermal and subdermal biofluids from living subjects.

BACKGROUND

Biomarker-based immunoassays are specific and quantitative; however, they depend on intradermal or subcutaneous extraction of fluid. One of the hurdles to intradermal extraction is the stratum corneum, namely, the uppermost layer of "dead skin." A means of bypassing the stratum corneum and extracting or probing interstitial fluid (ISF) would be an invaluable tool for the development of, for example, real-time health monitors.

Exemplary interstitial fluid (ISF) extraction employs chemical injection, sonophoresis, iontophoresis, Venturi chip/suction, or hollow microneedles. Each technique has significant disadvantages. Chemical injection is invasive and dilutes the extracted ISF. Sonophoresis requires vacuum suction and has high power consumption. Iontophoresis also has high power consumption, and it has poor depth control and extracts a limited volume of ISF. Venturi chip/suction requires removal of skin and may result in blister formation. Because of these disadvantages, none are suitable for long-term use in, for example, a wearable biosensor.

SUMMARY

In one embodiment, the disclosure provides a microneedle array including a plurality of microneedles that include nanocellulose or a nanocellulose composite.

In another embodiment, the disclosure provides a method of producing a microneedle array including casting a microneedle array by applying a nanocellulose or nanocellulose composite slurry to a microneedle mold and extracting the microneedle array from the microneedle mold.

In yet another embodiment, the disclosure provides a device including a microneedle array that include nanocellulose or a nanocellulose composite and a sorbent film connected to the microneedle array.

In yet another embodiment, the disclosure provides a method of extracting a dermal biofluid or subdermal biofluid from a living subject having a stratum corneum, including applying a microneedle array that includes nanocellulose or a nanocellulose composite to a region of skin of the living subject, penetrating the stratum corneum of skin with the microneedle array, and extracting a dermal biofluid or subdermal biofluid from the living subject with the microneedle array without mechanical or chemical pumping.

Other aspects of the invention will become apparent by consideration of the detailed description and accompanying drawings.

DETAILED DESCRIPTION

The disclosure generally provides for, among other things, arrays and devices comprising nanocellulose or nanocellulose composites, as well as methods of making and using the same.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The term "nanocellulose" refers to cellulose in which at least one dimension (namely, height, width, or length) is on the nanoscale. Nanoscale may be defined as less than 1000 or less than about 1000 nanometers. For example, nanoscale may be less than about 900, less than about 800, less than about 700, less than about 600, less than about 500, less than about 400, less than about 300, less than about 200, less than about 100, less than about 90, less than about 80, less than about 70, less than about 60, less than about 50, less than about 40, less than about 30, less than about 20, less than about 10, less than about 9, less than about 8, less than about 7, less than about 6, less than about 5, less than about 4, less than about 3, less than about 2, or less than about 1 nm. This includes a nanoscale of about 900, about 800, about 700, about 600, about 500, about 400, about 300, about 200, about 100, about 90, about 80, about 70, about 60, about 50, about 40, about 30, about 20, about 10, about 9, about 8, about 7, about 6, about 5, about 4, about 3, about 2, or about 1 nm. Nanoscale may include ranges of about 1 to about 5, about 1 to about 10, about 1 to about 100, about 1 to about 1000, about 20 to about 100, about 30 to about 100, about 40 to about 100, or about 50 to about 100 nm.

The term "nanocellulose composite" means a composition comprising nanocellulose and a polymer, biopolymer, biomacromolecules, proteins, or combination thereof. Examples of polymers, biopolymers, biomacromolecules, or proteins include, but are not limited to, hyaluronic acid (HA), poly(lactic-co-glycolic acid), poly(ethylene glycol), gelatin, collagen, alginate, chitosan, and (2,2,6,6-tetramethyl-piperidin-1-yl)oxyl (TEMPO) oxidized nanocellulose.

"Composite" has a meaning well understood in the art, such as, for example, a material made of two or more constituent materials where the individual components remain distinct within the combined structure. The components of the nanocellulose composites may be covalently linked, ionically linked, physically blended, orthogonally assembled or a combination thereof.

The ratio of nanocellulose to polymer, biopolymer, biomacromolecule, protein, or combination thereof may be 100% nanocellulose to 100% polymer, biopolymer, biomacromolecule, protein or combination thereof, including multiple intermediate composites thereof. For example, the ratio of nanocellulose to polymer, biopolymer, biomacromolecule, protein, or combination thereof may be about 99:1, about 95:5, about 90:10, about 85:15, about 80:20, about 75:25, about 70:30, about 65:35, about 60:40, about 55:45, about 50:50; about 45:55, about 40:60, about 35:65, about 30:70, about 25:75, about 20:80, about 15:85, about 10:90, about 5:95, or about 1:99.

The term "crystalline nanocellulose" refers to nanocellulose in the crystalline phase.

The term "semi-crystalline nanocellulose" refers to nanocellulose in a semi-crystalline phase.

The term "cellulose nanofiber" refers to a material composed of nanosized cellulose fibrils with a high aspect ratio (length to width ratio), for example, about 5 to about 100 nm with a wide range of lengths, typically greater than about 1 µm.

The term "bacterial nanocellulose" refers to nano-structured cellulose produced by bacteria, prokaryotic cells, co-cultures of prokaryotic and eukaryotic cells, and combinations thereof.

The terms "comprise(s)", "include(s)", "having", "has", "can", "contain(s)", and variants thereof, as used herein, are intended to be open-ended transitional phrases, terms, or words that do not preclude the possibility of additional acts or structures. The singular forms "a", "and", and "the" include plural references unless the context clearly dictates otherwise. The present disclosure also contemplates other embodiments "comprising", "consisting of", and "consisting essentially of", the embodiments or elements presented herein, whether explicitly set forth or not.

The conjunctive term "or" includes any and all combinations of one or more listed elements associated by the conjunctive term. For example, the phrase "an apparatus comprising A or B" may refer to an apparatus including A where B is not present, an apparatus including B where A is not present, or an apparatus where both A and B are present. The phrase "at least one of A, B, . . . and N" or "at least one of A, B, . . . N, or combinations thereof" are defined in the broadest sense to mean one or more elements selected from the group comprising A, B, . . . and N, that is to say, any combination of one or more elements A, B, . . . or N including any one element alone or in combination with one or more of the other elements, which may also include, in combination, additional elements not listed.

The modifier "about" used in connection with a quantity is inclusive of the stated value and has the meaning dictated by the context (for example, it includes at least the degree of error associated with the measurement of the particular quantity). The modifier "about" should also be considered as disclosing the range defined by the absolute values of the two endpoints. For example, the expression "from about 2 to about 4" also discloses the range "from 2 to 4". The term "about" may refer to plus or minus 10% of the indicated number. For example, "about 10%" may indicate a range of 9% to 11%, and "about 1%" may mean from 0.9-1.1. Other meanings of "about" may be apparent from the context, such as rounding off, so, for example "about 1" may also mean from 0.5 to 1.4.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

Arrays and Devices

It should be kept in mind that the following described embodiments are only presented by way of example and should not be construed as limiting the inventive concept to any particular physical configuration.

The disclosure provides for materials system designs for microneedle-based arrays and devices that can passively extract dermal and subdermal biofluids from a body or living subject. Conventional microneedles used as conduits for fluid are hollow and may be made of rigid materials (e.g., ceramic or metal systems) that require use of mechanical or chemical pumping. In other words, these microneedles are attached to a pump to withdraw fluid.

Different solutions have been proposed to overcome this barrier to assay interstitial fluid (ISF), but wearable biofluid extraction requires some form of active pumping. This is a significant technological hurdle. There is currently a lack of microneedle arrays able to absorb and transport intradermal fluids without the application of suction. Minimally-invasive and passive extraction of subcutaneous fluid will enable a myriad new biosensor and diagnostic technologies.

The microneedle arrays of the disclosure may employ materials and systems comprising nanocellulose, nanocellulose composites, or a combination thereof. In one aspect, the present disclosure relates to a microneedle array comprising a plurality of microneedles comprising nanocellulose or a nanocellulose composite. Without being limited by theory, the use of nanocellulose or nanocellulose composites may enable the passive extraction of subcutaneous fluids. Examples of nanocellulose may include, but are not be limited to, crystalline nanocellulose, semi-crystalline nanocellulose, cellulose nanofibers, microfibrillated cellulose, bacterial nanocellulose, wood-based nanocellulose, or a combination thereof. Ideally, the nanocellulose and nanocellulose composites have at least one of controllable porosity (e.g., about 0.01 to about 0.99), chemical stability (e.g., insoluble in aqueous solvents and/or polar organic solvents), and mechanical strength (e.g., elastic modulus from about 1 MPa to about 1000 MPa) such that conventional micromolding and fabrication of microneedles can be conducted.

The porosity of nanocellulose or a nanocellulose composite according to the present disclosure may be from about 0.01 to about 0.99, about 0.05 to about 0.99, about 0.1 to about 0.99, about 0.2 to about 0.99, about 0.3 to about 0.99, about 0.4 to about 0.99, about 0.5 to about 0.99, about 0.6 to about 0.99, about 0.7 to about 0.99, about 0.8 to about 0.99, about 0.9 to about 0.99, about 0.95 to about 0.99, about 0.01 to about 0.95, about 0.01 to about 0.9, about 0.01 to about 0.8, about 0.01 to about 0.7, about 0.01 to about 0.6, about 0.01 to about 0.5, about 0.01 to about 0.4, about 0.01 to about 0.3, about 0.01 to about 0.2, about 0.01 to about 0.1, about 0.01 to about 0.05, about 0.05 to about 0.95, about 0.1 to about 0.9, about 0.2 to about 0.8, about 0.3 to about 0.7, about 0.4 to about 0.6, or about 0.45 to about 0.55. This includes a porosity of at least 0.01, at least 0.05, at least 0.1, at least 0.2, at least 0.3, at least 0.4, at least 0.5, at least 0.6 at least 0.7, at least 0.8, at least 0.9, or at least 0.95. The porosity may be less than 0.1, less than 0.99, less than 0.95, less than 0.90, less than 0.85, less than 0.80, less than 0.75, less than 0.70, less than 0.65, less than 0.60, less than 0.55, less than 0.50, or less than 0.45.

The elastic modulus of nanocellulose or a nanocellulose composite according to the present disclosure may be from about 1 to about 1000, about 10 to about 1000, about 50 to about 1000, about 100 to about 1000, about 200 to about 1000, about 300 to about 1000, about 400 to about 1000, about 500 to about 1000, about 600 to about 1000, about 700 to about 1000, about 800 to about 1000, about 900 to about 1000, about 950 to about 1000, about 1 to about 950, about 1 to about 900, about 1 to about 800, about 1 to about 700, about 1 to about 600, about 1 to about 500, about 1 to about 400, about 1 to about 300, about 1 to about 200, about 1 to about 100, about 1 to about 50, about 1 to about 10, about 50 to about 950, about 100 to about 900, about 200 to about 800, about 300 to about 700, about 400 to about 600, or about 450 to about 550 MPa. This includes an elastic modulus of at least 1, at least 10, at least 20, at least 50, at least 100, at least 200, at least 500, or at least 900 MPa. The elastic modulus may be less than 1000, less than 900, less than 800, less than 700, less than 600, less than 500, less than 400, less than 300, less than 200, less than 100, less than 50, less than 20, less than 10, less than 5, or less than 2 MPa.

In some embodiments, the plurality of microneedles as disclosed herein include a nanocellulose composite, and the nanocellulose composite includes a polymer such as hyaluronic acid, poly(lactic-co-glycolic acid), poly(ethylene glycol), gelatin, alginate, chitosan, (2,2,6,6-tetramethyl-piperidin-1-yl)oxyl oxidized nanocellulose, or a combination thereof.

In some embodiments, at least one of the plurality of microneedles as disclosed herein is a hollow microneedle.

In some embodiments, at least one of the plurality of microneedles as disclosed herein has a diameter from about 100 μm to about 1000 μm, including, but not limited to, about 150 μm, about 200 μm, about 250 μm, about 300 μm, about 350 μm, about 400 μm, about 450 μm, about 500 μm, about 550 μm, about 600 μm, about 650 μm, about 700 μm, about 750 μm, about 800 μm, about 850 μm, about 900 μm, and about 950 μm. This include a diameter of at least 100, at least 200, at least 300, at least 400, at least 500, at least 600, at least 700, at least 800, or at least 900 μm. The diameter may be less than 1000, less than 900, less than 800, less than 700, less than 600, less than 500, less than 400, less than 300, or less than 200 μm, In some embodiments, at least one of the plurality of microneedles as disclosed herein has a tip width of less than or equal to about 10 μm. For example, the tip width may be less than or equal to about 9.5 μm, about 9.0 μm, about 8.5 μm, about 8.0 μm, about 7.5 μm, about 7.0 μm, about 6.5 μm, about 6.0 μm, about 5.5 μm, about 5.0 μm, about 4.5 μm, about 4.0 μm, about 3.5 μm, about 3.0 μm, about 2.5 μm, about 2.0 μm, about 1.5 μm, or about 1.0 μm. This includes a tip width of at least 1.0, at least 2.0, at least 3.0, at least 4.0, at least 5.0, at least 6.0, at least 7.0, at least 8.0, or at least 9.0 μm. The tip width may be less than 10.0, less than 9.0, less than 8.0, less than 7.0, less than 6.0, less than 5.0, less than 4.0, less than 3.0, or less than 2.0 μm.

In some embodiments, at least one of the plurality of microneedles as disclosed herein is pyramidal, having a base dimension and a height. For example, the base dimension may be about 500 μm by about 500 μm, about 450 μm by about 450 μm, about 400 μm by about 400 Gm, about 350 μm by about 350 μm, about 300 μm by about 300 μm, about 250 μm by about 250 μm, about 200 μm by about 200 μm, about 150 μm by about 150 μm, or about 100 m by about 100 μm. This includes a base dimension of at least 100 μm by 100 μm, at least 200 μm by 200 μm, at least 300 μm by 300 μm, at least 400 μm by 400 μm, or at least 450 μm by 450 μm. The base dimension may be less than 500 μm by 500 μm, less than 400 μm by 400 μm, less than 300 μm by 300 μm, less than 200 μm by 200 μm, or less than 150 μm by 150 μm. For example, the height may be about 1000 μm, about 900 μm, about 800 μm, about 700 μm, about 600 μm, about 500 μm, about 400 μm, or about 300 μm. This includes a height of at least 200 μm, at least 300 μm, at least 400 μm, at least 500 μm, at least 600 μm, at least 700 μm, at least 800 μm, or at least 900 μm. The height may be less than 1000 μm, less than 900 μm, less than 800 μm, less than 700 μm, less than 600 μm, less than 500 μm, less than 500 μm, or less than 300 μm. In some embodiments, the microneedles have a base dimension of about 250 μm by about 250 μm and a height of about 500 μm.

In some embodiments, at least one of the plurality of microneedles as disclosed herein is conical, having a base radius and a height. For example, the base radius of the conical microneedles may be about 500 μm, about 450 μm, about 400 μm, about 350 μm, about 300 μm, about 250, about 200 μm, about 150 μm, or about 100 μm. This includes a base radius of at least 100 μm, at least 200 μm, at least 300

μm, at least 400 μm, or at least 450 μm. The base radius may be less than 500 μm, less than 400 μm, less than 300 μm, less than 200 μm, or less than 150 μm. For example, the height of the conical microneedles may be about 1000 μm, about 900 μm, about 800 μm, about 700 μm, about 600 μm, about 500 μm, about 400 μm, or about 300 μm. This includes a height of at least 200 μm, at least 300 μm, at least 400 μm, at least 500 μm, at least 600 μm, at least 700 μm, at least 800 μm, or at least 900 μm. The height may be less than 1000 μm, less than 900 μm, less than 800 μm, less than 700 μm, less than 600 μm, less than 500 μm, less than 500 μm, or less than 300 μm. In some embodiments, the of the conical microneedles have a base radium of about 250 μm and a height of about 500 μm.

In some embodiments, the nanocellulose or nanocellulose composite as disclosed herein has a fibril density of at least 0.01 g/mL, including, but not limited to, from about 0.01 to about 10 g/mL, from about 0.01 to about 5 g/mL, from about 0.01 to about 2.5 g/mL, from about 0.01 to about 1.5 g/mL, or from about 0.01 to about 0.9 g/mL. For example, the fibril density may range from about 0.05 to about 0.8 g/mL, from about 0.10 to about 0.7 g/mL, from about 0.15 to about 0.6 g/mL, or from about 0.20 to about 0.5 g/mL. This includes a fibril density of at least 0.01 g/mL, at least 0.02 g/mL, at least 0.05 g/mL, at least 0.10 g/mL, at least 0.20 g/mL, at least 0.50 g/mL, at least 1.00 g/mL, at least 1.20 g/mL, at least 1.50 g/mL, at least 2.00 g/mL, or at least 5.00 g/mL, or at least 9.00 g/mL. The fibril density may be less than 9.50 g/mL, less than 8.00 g/mL, less than 7.00 g/mL, less than 6.00 g/mL, less than 5.00 g/mL, less than 4.00 g/mL, less than 3.00 g/mL, less than 2.00 g/mL, less than 1.00 g/mL, less than 0.50 g/mL, less than 0.20 g/mL, less than 0.10 g/mL, less than 0.05 g/mL, or less than 0.02 g/mL.

In some embodiments, the nanocellulose or nanocellulose composite as disclosed herein has a fibril thickness of from about 10 nm to about 1 μm. For example, the fibril thickness may be about 10 nm, about 20 nm, about 30 nm, about 40 nm, about 50 nm, about 60 nm, about 70 nm, about 80 nm, about 90 nm, about 100 nm, about 200 nm, about 300 nm, about 400 nm, about 500 nm, about 600 nm, about 700 nm, about 800 nm, about 900 nm, or about 1 μm. This includes a fibril thickness of at least 10 nm, at least 20 nm, at least 30 nm, at least 40 nm, at least 50 nm, at least 60 nm, at least 70 nm, at least 80 nm, at least 90 nm, at least 100 nm, at least 200 nm, at least 300 nm, at least 400 nm, at least 500 nm, at least 600 nm, at least 700 nm, at least 800 nm, or at least 900 nm. The fibril thickness may be less than 950 nm, less than 900 nm, less than 800 nm, less than 700 nm, less than 600 nm, less than 500 nm, less than 400 nm, less than 300 nm, less than 200 nm, less than 100 nm, less than 90 nm, less than 80 nm, less than 70 nm, less than 60 nm, less than 50 nm, less than 40 nm, less than 30 nm, less than 20 nm, or less than 15 nm.

The microneedles as disclosed herein may have mechanical strength sufficient for penetrating the stratum corneum. In some embodiments, the microneedles may withstand a compressive load of at least about 15 N without breaking as measured by known mechanical testing methods. For example, the microneedles may withstand a compressive load of about 15 N, about 16N, about 17 N, about 18 N, about 19 N, about 20 N, about 21 N, about, 22 N, about 23 N, about 24 N, or about 25 N without breaking. This includes a compressive load of at least 10 N, at least 12 N, at least 14 N, at least 16 N, at least 18 N, at least 20 N, at least 22 N, or at least 24 N. The compressive load may be less than 25 N, less than 23 N, less than 21 N, less than 19 N, less than 17 N, less than 15 N, less than 13 N, or less than 11 N.

In another aspect, the present disclosure may provide a method of producing a microneedle array comprising, the method comprising: a) casting a microneedle array by applying a nanocellulose or nanocellulose composite slurry to a microneedle mold; and b) extracting the microneedle array from the microneedle mold.

In some embodiments, the disclosed method of producing a microneedle array may further comprise: a1) drying the cast microneedle array of a) under controlled temperature and humidity; and a2) in situ crosslinking the microneedle array of a1) before the extraction of b).

For example, the disclosed method of producing a microneedle array may include the steps of: a) casting a microneedle array by applying a nanocellulose or nanocellulose composite slurry to a microneedle mold; a1) drying the cast microneedle array of a) under controlled temperature and humidity; a2) in situ crosslinking the microneedle array of a1); and b) extracting the microneedle array from the microneedle mold. In general, the drying process of a1) controls the porosity and performance of the microneedles. The drying process of a1) and the crosslinking process of a2) may be carried out under conditions know in the art.

In some embodiments, the method of producing a microneedle array further comprises attaching the microneedle array to a stretchable backing film.

In another aspect, the present disclosure provides a device comprising: a) a microneedle array comprising a plurality of microneedles comprising nanocellulose or a nanocellulose composite as disclosed herein; and b) a sorbent film connected to the microneedle array.

In some embodiments, the sorbent film comprises hyaluronic acid, polyvinyl alcohol, polyethylene glycol, a biocompatible sorbent, or a combination thereof.

In some embodiments, the sorbent film connected to the microneedle array controls the flow of fluid through the microneedle array via passive sample collection and capillary force.

In some embodiments, the device further comprises a biosensor for detecting or measuring an analyte from a fluid. For example, the fluid may be extracted by the microneedles and subsequently analyzed by the biosensor.

In some embodiments, the device as disclosed herein is capable of detecting or measuring the analyte continuously for at least a duration of time greater than about 10 minutes without mechanical or chemical pumping. For example, the analyte may be an analyte in the fluid under the skin of a subject. The fluid may be extracted by the microneedles and subsequently analyzed by the biosensor of the device, and the analysis may be conducted in a continuous manner without any additional mechanisms (such as mechanical or chemical pumping) to facilitate the extraction of the fluid by the microneedles. The duration of such continuous analysis may be at least 10 minutes, at least 20 minutes, at least 30 minutes, at least 60 minutes, or at least 120 minutes.

Method of Use

The nanocellulose or nanocellulose composite may be applicable to nearly any use requiring the extraction of subsurface biofluids for analysis. For example, the exemplary arrays and devices comprising nanocellulose and nanocellulose composites may be optimal for application to skin or other biological tissue because they are bio-compatible or oxygen permeable, or provide for wicking (high water permeation). Such applications include, but are not limited to, extraction of biofluids such as sweat, ISF, subcutaneous fluid, and blood from subcutaneous regions of skin (e.g., epidermis or dermis). The devices and microneedle arrays as disclosed herein may be biocompatible and may transmit biofluids from the tissue to an attached bioelectronic sensor or device by passive fluid absorption, such as capillary or osmotic flow. Because such fluids are under a negative pressure, they typically require some type of active pumping for extraction. The disclosed systems, in contrast, can circumvent the need for any active pumping, such as mechanical or chemical pumping, for example.

In one aspect, the present disclosure provides method of extracting a dermal biofluid or subdermal biofluid from a living subject having a stratum corneum, the method comprising: a) applying a microneedle array comprising nanocellulose or a nanocellulose composite to a region of skin of the living subject; b) penetrating the stratum corneum of skin with the microneedle array; and c) extracting a dermal biofluid or subdermal biofluid from the living subject with the microneedle array without mechanical or chemical pumping.

In certain embodiments, the disclosed systems may be used for sample collection or as a handling component of wearable biosensors. The disclosed systems may also be used for sample separation in wearable biosensors, for example, and it may serve a similar role in implantable or ex vivo tissue analysis.

In some embodiments, the method disclosed herein further comprises analyzing the biofluid with an immunoassay. For example, the dermal biofluid or subdermal biofluid from the living subject extracted in step c) may be subsequently analyzed by a sensor capable of detecting and/or measuring the concentration of a particular analyte (such as a target peptide or antibody) through immunoreaction.

Figure 1:
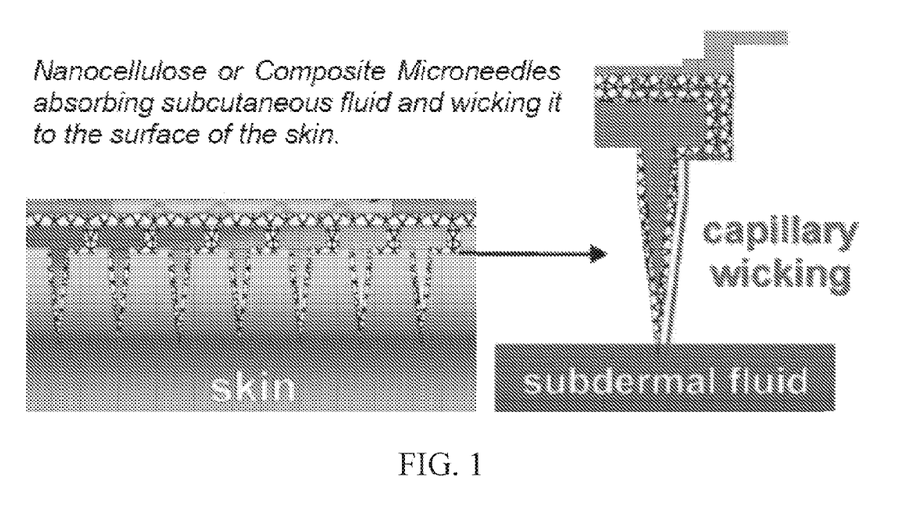
FIG. 1 is a schematic representation of the working principle for a nanocellulose or composite microneedle array to extract and transport intradermal fluids. The solid, yet compliant microneedles can enable long-term penetration of the skin. The nanocellulose-coating is a biocompatible interface between the microneedle and skin, enabling the passive extraction of intradermal fluid by capillary force and diffusion.

In some embodiments, the method disclosed herein further comprises continuously extracting a subcutaneous fluid from the living subject for at least a duration of time greater than about 10 min. The exemplary nanocellulose and nanocellulose composites described herein are designed to provide optimal material functionality for supporting continuous extraction of subcutaneous fluid by, for example, capillary action or wetting (FIG. 1). The continuous extraction of subcutaneous fluid may have a duration greater than or equal to about 1 min, about 10 min, about 20 min, about 30 min, about 45 min, about 1 hr, about 2 hr, about 4 hr, about 6 hr, about 8 hr, about 10 hr, about 12 hr, about 18 hr, about 1 day, about 2 days, about 3 days, about 4 days, about 5 days, about 6 days, about 1 wk, about 2 wk, about 3 wk, or about 1 mo.

The disclosed materials and systems for fabrication of microneedle arrays to extract subcutaneous fluid improve upon many systems currently being used in research and industry. One novel aspect of the disclosed systems is the implementation of an unconventional nanomaterial to enable the required porosity (e.g., as measured by electron microscopy and/or water swelling uptake, the water swelling preferably greater than 400 wt %), wetting (e.g., as measured by goniometry, preferably having aqueous contact angles less than about 90°), capillary action, and/or mechanical strength (e.g., as measured by tensile and/or compression testing, preferably having an elastic modulus greater than about 1 MPa and less than about 1000 MPa) to extract subcutaneous fluid. Microneedles nanocellulose or nanocellulose composites may provide at least one of the following advantages over existing alternatives.

The water swelling uptake of nanocellulose or a nanocellulose composite according to the present disclosure may be greater than or equal to about 100, about 150, about 200, about 250, about 300, about 350, about 400, about 450, about 500, about 550, about 600, about 650, about 700, about 750, about 800, about 850, about 900, about 950, or about 1000 wt %.

The wettability of nanocellulose or a nanocellulose composite according to the present disclosure, as measured by goniometry, may have aqueous contact angles less than or equal to about 120, about 115, about 110, about 105, about 100, about 90, about 85, about 80, about 75, about 70, about 65, about 60, about 55, about 50, about 45, about 40, about 35, about 30, about 25, about 20, about 15, about 10, or about 5 degrees.

The disclosed microneedles comprising nanocellulose and nanocellulose composites may provide advantageous properties (such as porosity, wetting, capillary action, mechanical strength) to enable extract subcutaneous fluid, which cannot be achieved by conventional materials.

(1) Substrate properties that are optimal for application to dermal tissue, for example, water and oxygen permeability (e.g., as measured by Paddington Cup methods, with a Water Vapor Transmission rate preferably greater than about 500 $g/cm^2/day$), as well as mechanical robustness (e.g., as measured by tensile and/or compression testing, with no failure observed) and chemical robustness (e.g., the materials are insoluble in aqueous and/or polar solvents). These properties also make the nanocellulose and nanocellulose composite substrates an excellent choice for biochemical sensors, which rely on the transmission of biochemicals present at the biological tissue surface.

The water permeability of nanocellulose or a nanocellulose composite according to the present disclosure may be greater than or equal to about 50.

(2) Ability to use conventional fabrication techniques such as micro-molding or casting for making the microneedles. Fabrication, however, can be done by many methods other than casting or micro-molding, such as spray deposition and dip coating, for example. Also, any suitable type of device manufacturing process can be used, if the technique stays below the degradation temperature and within chemical compatibility of the nanocellulose or nanocellulose composites.

(3) Cost-effectiveness in terms of use of materials that are ubiquitous biomass products, which may also provide enhanced sustainability over existing alternatives. There are many sources for nanocellulose, including bacterial, tunicate, plant, and other types of biomass, for example. The composite constituents also have a broad availability, but certain parameters should be kept in mind, such as biocompatibility and chemical stability.

(4) Systems that may be completely passive: no mechanical or chemical pumping mechanism is required.

Example 1—Fabrication of Microneedle Array

Microneedle arrays were fabricated by micro-molding and casting the materials. The microneedle arrays were integrated into a stretchable backing film for further functionality. Independent processing steps, which may be readily apparent to one of skill in the art, controlled the microneedle size, density, and shape. For example, by controlling the drying and evaporation rate of the cast nanocellulose or nanocellulose composites, the porosity, geometry, density, and shape could be controlled: rapid drying of casts under vacuum and elevated temperature resulted in hollow microneedles with increased density and mechanical stiffness; casting under increased humidity and centrifugal force, followed by slow drying (at room temperature for about 24 hr) resulted in solid microneedles with increased porosity.

The microneedle arrays were cast from a series of suitable polymers, including hyaluronic acid (HA), poly(lactic-co-glycolic acid), and (2,2,6,6-tetramethyl-piperidin-1-yl)oxyl (TEMPO), to form nanocellulose composites. The series ranged from 100% TEMPO-oxidized nanocellulose—from the University of Maine or microbial nanocellulose produced in-house—to 100% polymer, including multiple intermediate composites thereof. For example, 50/50%, 25/75%, and 75/25% composites, among others, were fabricated.

Microneedle diameters for fluid sampling were as small as 100 μm. For example, the microneedle diameter may be less than or equal to about 1000, about 900, about 800, about 700, about 600, about 500, about 400, about 300, about 200, about or 100 μm. The microneedle diameter may be about 100 to about 1000, about 100 to about 900, about 100 to about 800, about 100 to about 700, about 100 to about 600, about 100 to about 500, about 100 to about 400, about 100 to about 300, or about 100 to about 200 μm.

During processing, the nanocellulose fibril density and thickness were optimized. Fibril density and thicknesses ranged from about 0.01 to about 0.9 g/mL and from about 1 to about 10 μm, respectively, although other fibril densities and thicknesses are possible. Microneedles having a thickness of from about 10 nm to about 1 μm were prepared by the process disclosed herein.

The microneedle arrays were integrated into a stretchable backing film that can be worn on the skin. Depending on the required flexibility and compliance, varied materials could be used for the stretchable backing film, such as hyaluronic acid, polyvinyl alcohol (PVA), polyethylene glycol (PEG), or other biocompatible sorbents.

Formation of Nanocellulose and Nanocellulose Composites into Microneedle Arrays.

Nanocellulose was selected for its high solubility, tunable viscosity, and high stiffness after casting. A nanocellulose slurry was cast into microneedle arrays. The microneedles were approximately pyramidal with a base dimension of about 250 μm×about 250 μm and a height of about 500 μm. The resultant nanocellulose microneedles exhibited a point sharpness (tip width) of about 10 μm and a substantial microscale porosity.

Mechanical Testing of Microneedle Arrays for Penetration of the Stratum Corneum.

Nanocellulose microneedle arrays were tested under compressive loading. The nanocellulose microneedle arrays (20 microneedles per test) exhibited failure at about 15 to about 20 N. Continued efforts will examine the mode of failure, as well as calculation of single needle strength.

Formation of Composites of Nanocellulose and Hyaluronic Acid into Microneedle Arrays.

To tune the stiffness of the microneedle arrays, nanocellulose was combined with hyaluronic acid. Hyaluronic acid (HA) is a biopolymer sometimes used to fabricate microneedles. Multiple compositions were fabricated and mechanical testing is underway. The ability to tune the stiffness of the microneedles will aid in engineering devices for different skin locations and duration of operation.

Figure 2:
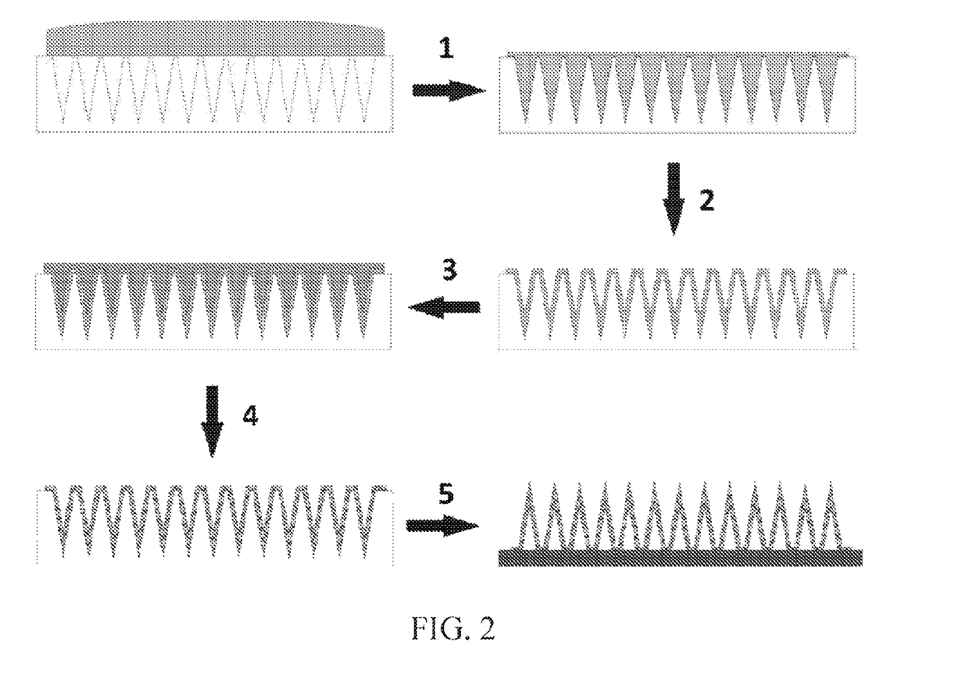
FIG. 2 is a schematic representation of a microneedle fabrication process according to the present disclosure.
Figure 3:
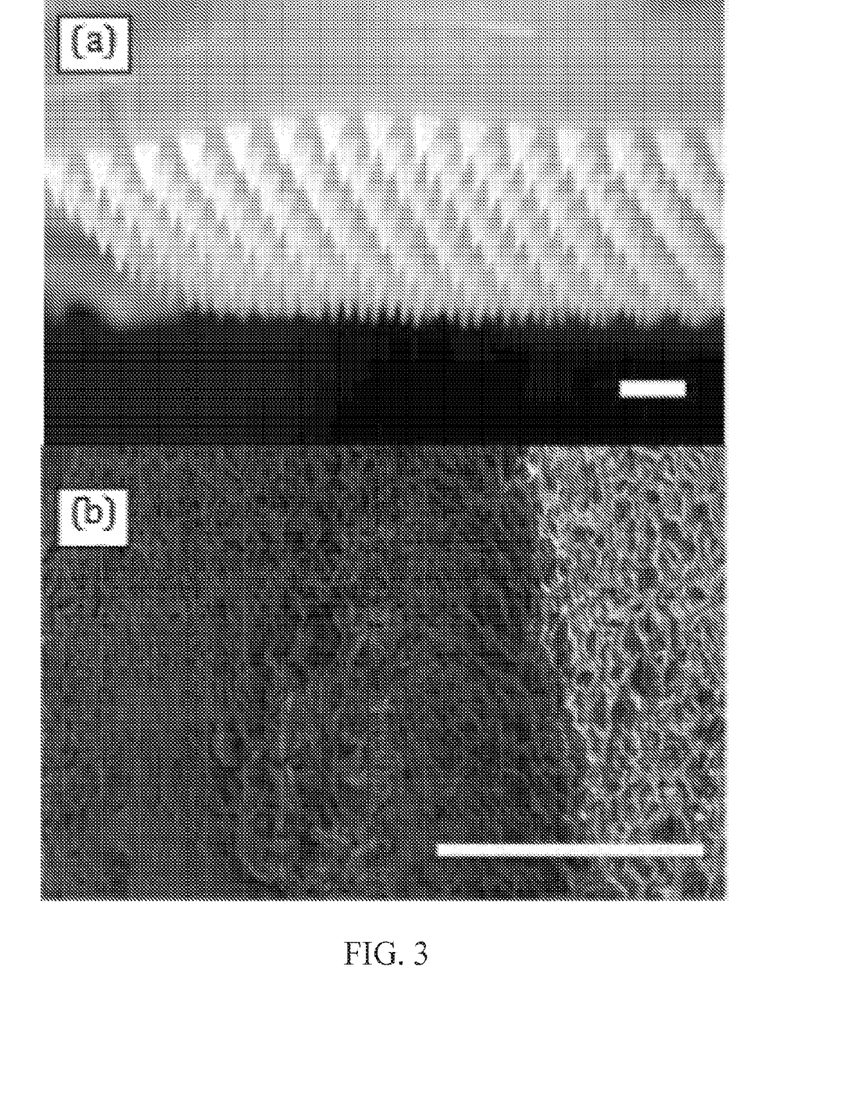
FIG. 3 is an (a) photograph of nanocellulose microneedle array (scale bar=1 mm), and an (b) electron micrograph of a nanocellulose microneedle array (scale bar=0.03 mm).
Figure 4:
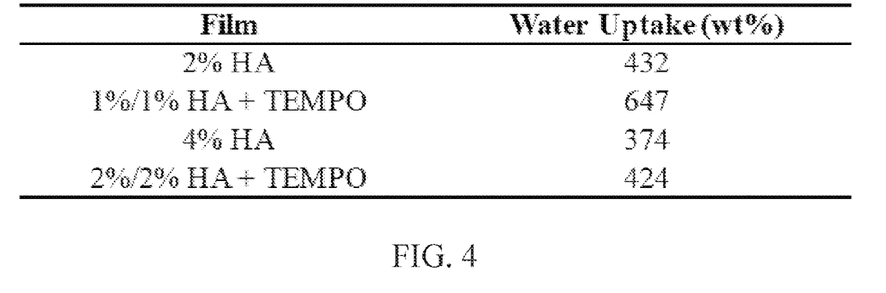
FIG. 4 shows water absorption of nanocellulose and nanocellulose composites used for microneedle arrays.
Figure 5:
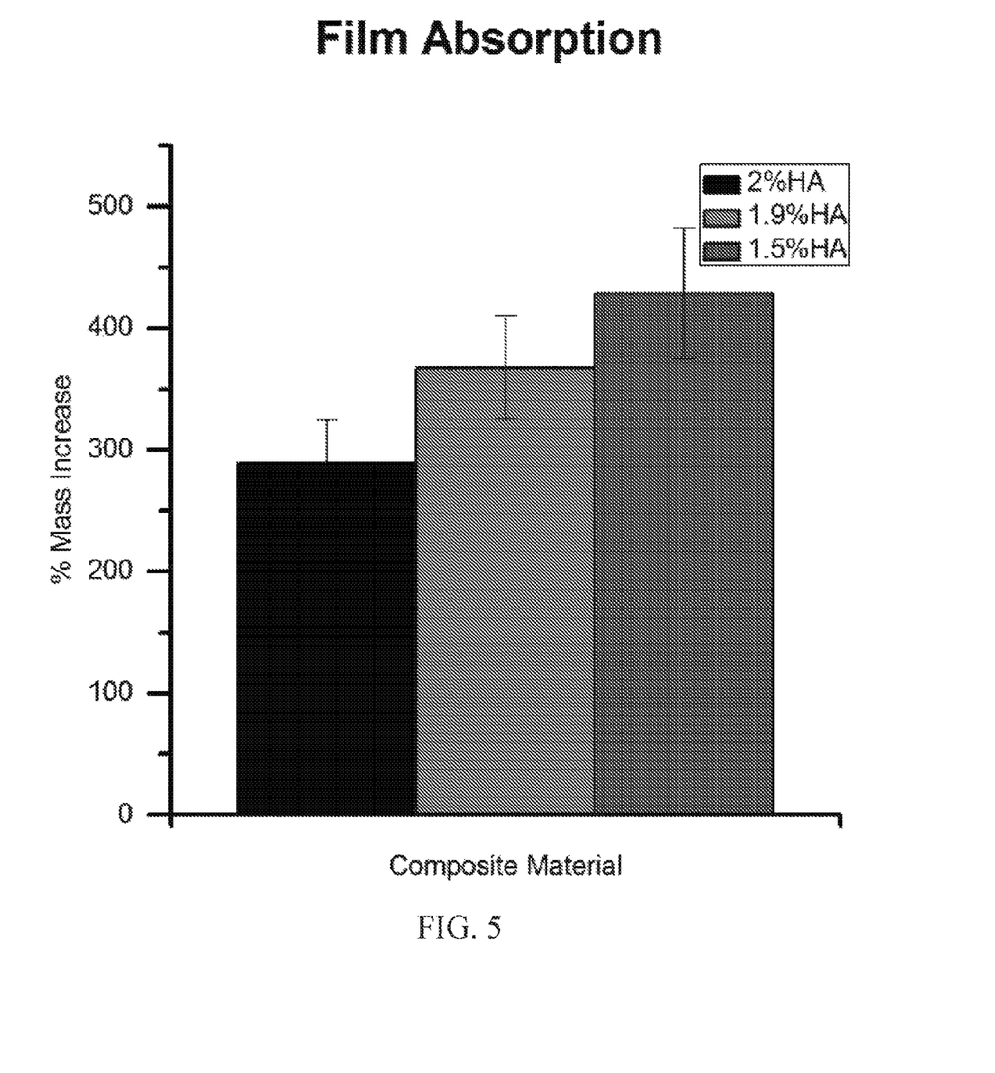
FIG. 5 shows thin film absorption properties of nanocellulose and composite materials used for microneedle arrays.
Figure 6:
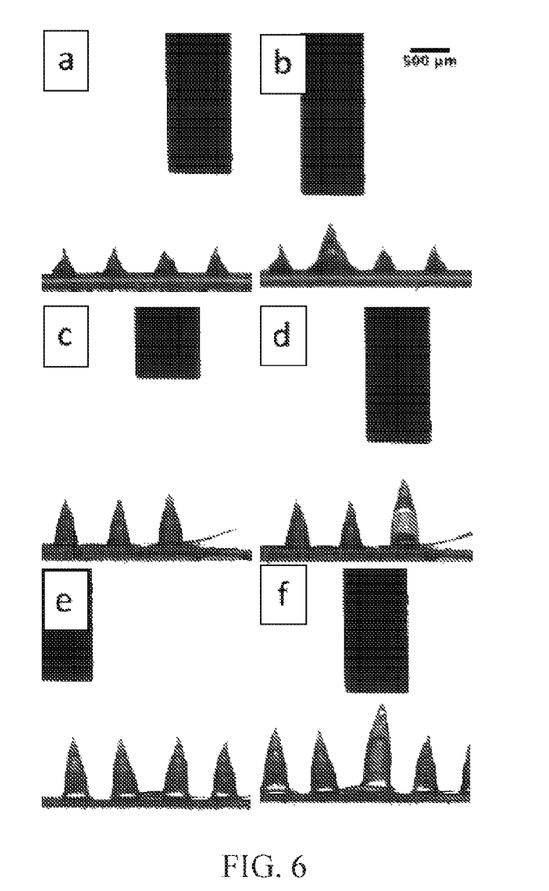
FIG. 6 shows representative swelling of individual microneedles from dry (left column) to swollen (right column).
Figure 7:
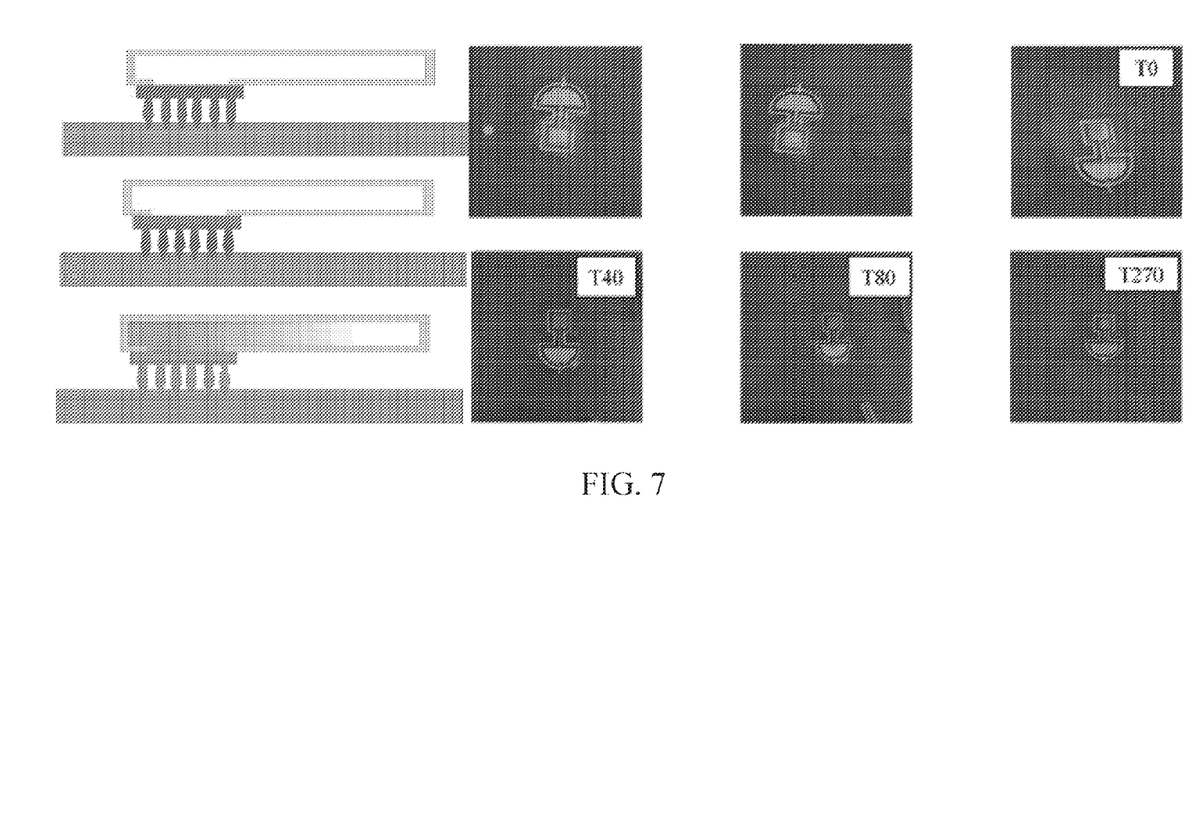
FIG. 7 shows a schematic representation of a sorbent backing design used for evaluation experiments (left), and time lapse photographs illustrating the transport of fluid across an impermeable membrane and into the sorbent backing via the disclosed microneedle technology (right).
Figure 8:
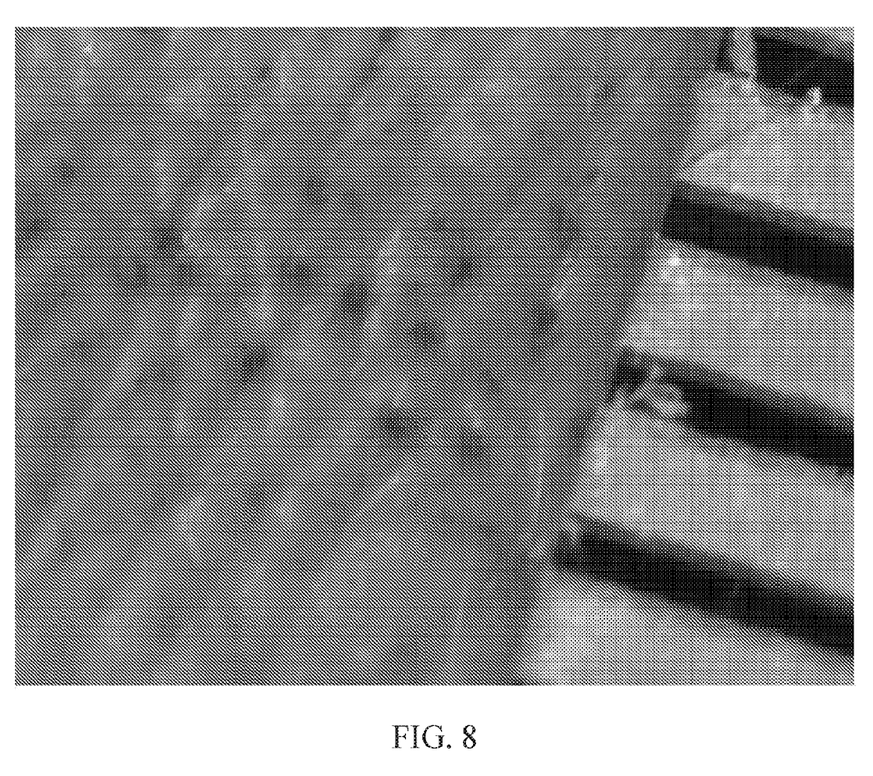
FIG. 8 shows skin puncture of human epidermis with hyaluronic acid (HA) microneedles.

An exemplary system is as follows (see FIG. 2):
1. Nanocellulose or composites thereof are prepared by mechanical homogenization;
2. The nanocellulose or composite material is diluted in water and cast into a microneedle mold;
3. After drying, the microneedle array is extracted from the mold and attached to a sorbent film;
4. The microneedle array is applied to the skin, and due to capillary, osmotic, or wetting forces, subcutaneous fluid is passively transported through the microneedle array to the sorbent film; and
5. Extracted fluids are analyzed.

In a more complex system, which has been reduced to practice, a nanocellulose composite system was used to absorb fluid and transport through a sorbent film (FIGS. 3-8).

Figure 9:
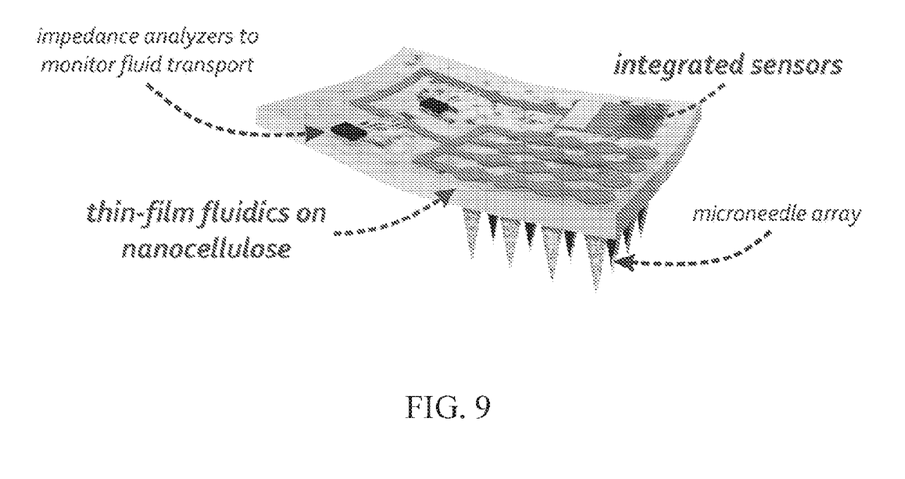
FIG. 9 shows a representative device including a microneedle array, thin-film fluidics on nanocellulose, impedance analyzers to monitor fluid transport, and integrated sensors.

An example device was manufactured, which included a microneedle array, thin-film fluidics on nanocellulose, impedance analyzers to monitor fluid transport, and integrated sensors (FIG. 9).

While specific configurations of the microneedle array have been described, it is understood that the present invention could take on a variety of other forms. Various features and advantages of the invention are set forth in the following claims.

What is claimed is:

1. A microneedle array comprising a plurality of microneedles comprising a crosslinked nanocellulose composite, wherein the nanocellulose composite comprises a permanently crosslinked composite of hyaluronic acid, poly (lactic-co-glycolic acid), poly(ethylene glycol), gelatin, alginate, chitosan, or a combination thereof.

2. The microneedle array of claim 1, wherein the nanocellulose composite is crystalline nanocellulose.

3. The microneedle array of claim 1, wherein at least one of the plurality of microneedles is a hollow microneedle, wherein at least one of the plurality of microneedles has a diameter from about 100μ·m to about 1000μ·m, wherein at least one of the plurality of microneedles has a tip width of less than or equal to about 10 μm.

4. The microneedle array of claim 1, wherein at least one of the plurality of microneedles is pyramidal with a base dimension of about 250μ·m by about 250μ·m and a height of about 500μ·m.

5. The microneedle array of claim 1, wherein the of crosslinked nanocellulose composite has a fibril density from about 0.01 to about 0.9 g/mL.

6. The microneedle array of claim 5, wherein the crosslinked nanocellulose composite has a fibril thickness of from about 10 nm to about 1μ·m.

7. The microneedle array of claim 1, wherein the plurality of microneedles is insoluble in an aqueous solvent, in a polar organic solvent, or a combination thereof.

8. The microneedle array of claim 1, wherein the plurality of microneedles has an elastic modulus from about 500 MPa to about 1000 MPa.

9. A microneedle array comprising a plurality of microneedles comprising crosslinked nanocellulose or a crosslinked nanocellulose composite, wherein the nanocellulose or nanocellulose composite comprises bacterial nanocellulose wherein the nanocellulose composite comprises a permanently crosslinked composite of hyaluronic acid, poly (lactic-co-glycolic acid), poly(ethylene glycol), gelatin, alginate, chitosan, or a combination thereof.

10. The microneedle array of claim 9, wherein the crosslinked nanocellulose composite has a fibril density from about 0.01 to about 0.9 g/mL and a fibril thickness of from about 10 nm to about 1μ·m, wherein the nanocellulose composite has an elastic modulus of about 500 to 1000 mPa, wherein the plurality of microneedles is insoluble in an aqueous solvent, wherein the nanocellulose composite comprises a permanently crosslinked composite of hyaluronic acid, poly(lactic-co-glycolic acid), poly(ethylene glycol), or a combination thereof.

11. The microneedle array of claim 1, wherein the nanocellulose composite is semi-crystalline nanocellulose.

12. The microneedle array of claim 1, wherein the nanocellulose composite is cellulose nanofibers.

13. The microneedle array of claim 1, wherein the nanocellulose composite is microfibrillated cellulose.

14. The microneedle array of claim 1, wherein the nanocellulose composite is bacterial nanocellulose.

15. The microneedle array of claim 1, wherein the nanocellulose composite is wood-based nanocellulose.

16. The microneedle array of claim 1, wherein the nanocellulose composite is a permanently crosslinked composite of hyaluronicacid.

17. The microneedle array of claim 1, wherein the nanocellulose composite is a permanently crosslinked composite of poly(lactic-co-glycolic acid).

18. The microneedle array of claim 1, wherein the nanocellulose composite is a permanently crosslinked composite of poly(ethylene glycol).

19. The microneedle array of claim 1, wherein the nanocellulose composite is a permanently crosslinked composite of alginate.

20. The microneedle array of claim 1, wherein the nanocellulose composite is a permanently crosslinked composite of chitosan.

* * * * *